United States Patent [19]

Freenor

[11] 3,965,218

[45] June 22, 1976

[54] PHOSPHOROAMIDOTHIOATES

[75] Inventor: Francis J. Freenor, Richmond, Calif.

[73] Assignee: Chevron Research Company, San Francisco, Calif.

[22] Filed: Apr. 7, 1975

[21] Appl. No.: 565,324

Related U.S. Application Data

[62] Division of Ser. No. 394,872, Sept. 6, 1973, Pat. No. 3,882,200.

[52] U.S. Cl. ............................... 260/941; 260/943
[51] Int. Cl.$^2$ ............................................ C07F 9/24
[58] Field of Search .......................... 260/941, 943

[56] References Cited
UNITED STATES PATENTS 3,113,958  12/1963  Miller et al. ....................... 260/941

*Primary Examiner*—Richard L. Raymond
*Attorney, Agent, or Firm*—G. F. Magdeburger; John Stoner, Jr.; Raymond Owyang

[57] ABSTRACT

Compounds of the formula

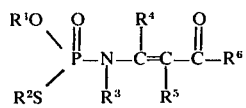

wherein $R^1$ and $R^2$ individually are alkyl or alkenyl; $R^4$ is hydrogen, alkyl or haloalkyl; $R^3$ and $R^5$ are hydrogen or alkyl and $R^6$ is alkyl, haloalkyl, aryl, alkoxy, aryloxy, alkylthio, or amino are produced by the acid-catalyzed condensation of a 1,3-dicarbonyl compound of the formula

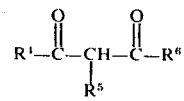

with a phosphoroamidothioate compound of the formula

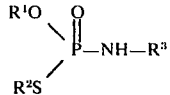

wherein $R^1$ and $R^6$ are as defined above. The compounds are highly active insecticides, with low mammalian toxicity.

9 Claims, No Drawings

PHOSPHOROAMIDOTHIOATES

This is a division of application Ser. No. 394,872, filed Sept. 6, 1973, now U.S. Pat. No. 3,882,200.

BACKGROUND OF THE INVENTION

U.S. Pat. Nos. 3,676,555 and 3,689,604 of G. Schrader et al disclose insecticidal O,S-dialkylphosphoroamidothioates. U.S. Pat. Nos. 3,649,723 and 3,716,600 of P. S. Magee disclose O-alkyl-S-unsaturated hydrocarbyl-(N-acyl)phosphoroamidothioates.

German application No. 2,716,690, published Oct. 19, 1972, of Farbenfabriken Bayer AG discloses insecticidal O,S-dialkyl-N-alkoxymethylene-(di)thiophosphoramidic acids. German application No. 2,118,469, published Oct. 26, 1972, of Farbenfabriken Bayer AG discloses N-(dimethylaminomethylene)thiolo(thiono)-phosphoric acid ester imides.

DESCRIPTION OF THE INVENTION

The insecticidal compounds of the invention are represented by the formula (I)

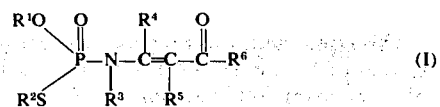

wherein $R^1$ is lower alkyl of 1 to 6 carbon atoms or lower alkenyl of 3 to 6 carbon atoms;

$R^2$ is lower alkyl of 1 to 6 carbon atoms or lower alkenyl of 3 to 6 carbon atoms;

$R^3$ is hydrogen or lower alkyl of 1 to 6 carbon atoms;

$R^4$ is hydrogen, lower alkyl of 1 to 6 carbon atoms, or lower haloalkyl of 1 to 6 carbon atoms and 1 to 3 halogens of atomic number 9 to 35;

$R^5$ is hydrogen or lower alkyl of 1 to 6 carbon atoms;

$R^6$ is lower alkyl of 1 to 6 carbon atoms, lower haloalkyl of 1 to 6 carbon atoms and 1 to 3 halogens of atomic numer 9 to 35, lower alkoxy of 1 to 6 carbon atoms, lower alkythio of 1 to 6 carbon atoms, phenyl, phenyl substituted with 1 to 2 alkyl of 2 to 4 carbons, fluorine, chlorine or bromine, phenoxy, phenoxy substituted with 1 to 2 alkyl of 1 to 4 carbon atoms, fluorine, chlorine or bromine, amino, N-lower alkylamino of 1 to 7 carbon atoms, N,N-di-lower alklamino of 2 to 10 carbon atoms, N-phenylamino or N-lower alkylphenylamino of 7 to 10 carbon atoms, with the proviso that two alkyl $R^4$ and $R^6$ groups may be joined to form a 5- or 6- carbocyclic ring (e.g., $R^4$ and $R^6$ are divalent alkylene groups such as dimethylene or trimethylene).

Additional insecticidal compounds of the invention are those wherein $R^1$ or $R^2$ are aryl, i.e., phenyl, aralkyl or alkaryl of 7 to 10 carbon atoms optionally substituted with up to 2 groups selected from fluorine, chlorine, bromine, alkoxy of 1 to 4 carbon atoms or nitro, and $R^3$, $R^4$, $R^5$ and $R^6$ are as defined above. Still other insecticidal compounds of the invention are those wherein $R^6$ is monocyclic aralkyl, alkaryl, aralkoxy, or alkaryloxy of 7 to 10 carbon atoms optionally substituted with up to 2 groups selected from fluorine, chlorine, bromine, alkoxy of 1 to 4 carbon atoms or nitro, and $R^1$, $R^2$, $R^3$, $R^4$ and $R^5$ are as defined above.

The preferred compounds of the invention are those wherein $R^6$ is alkoxy and $R^1$, $R^2$, $R^3$, $R^4$ and $R^5$ are as defined above. The particularly preferred compounds of the invention are those wherein $R^6$ is methoxy or ethoxy and $R^1$, $R^2$ and $R^4$ are alkyl of 1 to 6 carbon atoms, $R^3$ and $R^5$ are hydrogen.

The compounds of the invention are prepared by the acid-catalyzed condensation of a 1,3-dicarbonyl-containing compound and a phosphoroamidothioate compound, as depicted in the following equation (1)

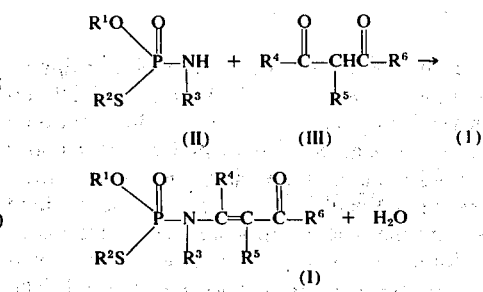

wherein $R^1$, $R^2$, $R^3$, $R^4$, $R^5$ and $R^6$ have the same significance as previously defined.

The reaction depicted in equation (1) is conducted in the presence of a catalytic amount of a strong acid. Suitable strong acids include inorganic acids such as sulfuric acid, halogen acids — e.g., hydrochloric acid, phosphoric acid, etc. — and organic acids such as arylsulfonic acids — e.g., p-toluenesulfonic acid and naphthylenesulfonic acid. The phosphoroamidothioate reactant (II) and the dicarbonyl reactant (III) generally are contacted in molar ratios of 1:2 to 2:1, although substantially equimolar ratios are preferred. The reaction is conducted in the liquid phase in inert solvents such as aromatic hydrocarbons — e.g., benzene, toluene, xylene, etc. — and alkanes — e.g., hexane, cyclohexane, isooctane, decane, etc. Suitable reaction temperatures vary from about 50° to 150°C. The product (I) is isolated and purified by conventional procedures such as filtration, extraction, chromatography.

Preparation of the compounds of the invention is illustrated by the following examples.

EXAMPLE 1

Preparation of O,S-dimethyl-N-3-ketopent-2-en-2-yl)-phosphoroamidothioate

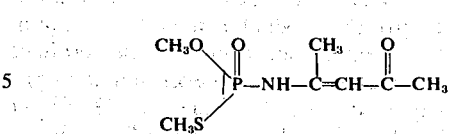

A solution of 12.65 g (0.09 mol) O,S-dimethylphosphoroamidothioate, 9 g (0.09 mol) acetylacetone, 5 drops concentrated sulfuric acid and 300 ml benezene was heated reflux for 4 hours in a flask equipped with a Dean-Stark trap. The benzene/water in the Dean-Stark trap was discarded. The reaction mixture was then evaporated to give the product as a yellow oil. Thin-layer chromatography showed the product to be substantially homogeneous. The infrared spectrum of the product showed α,β-unsaturated carbonyl absorption at 6.1μ. Elemental analysis showed: %S, calc. 14.38, found 14.08; %P, calc. 13.85, found 13.22.

EXAMPLE 2

Preparation of
O,S-dimethyl-N-[1-(N',N'-diethylcarbamyl)prop-1-en-2-yl]phosphoroamidothioate

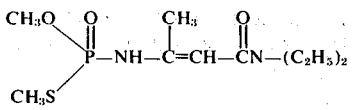

A solution of 7.58 g (0.054 mol) O,S-dimethylphosphoroamidothioate, 8.44 g (0.054 mol) 1-(N,N-diethylcarbamyl)-2-propanone, 0.1 g p-toluenesulfonic acid and 500 ml benzene was heated 6 hours under reflux in a flask equipped with a Dean-Stark trap. Three drops of concentrated sulfuric acid were added to the flask and the reaction mixture was heated under reflux an additional 2 hours. The reaction mixture was evaporated to give the product as a yellow oil. The infrared spectrum of the product showed α,β-unsaturated carbonyl absorption at 6.1μ. Elemental analysis showed: %S, calc. 11.45; found 10.88.

EXAMPLE 3

Preparation of
O,S-dimethyl-N-[1-carbo-t-butoxy)prop-1-en-2-yl]phosphoroamidothioate

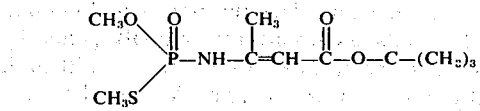

A solution of 7.6 g (0.054 mol) O,S-dimethylphosphoroamidothioate, 8.5 g (0.054 mol) 1-carbo-t-butoxypropan-2-one, 0.1 g p-toluenesulfonic acid and 500 ml benzene was heated under reflux for 4 hours in a flask equipped a Dean-Stark trap. Analysis of the reaction mixture by thin-layer chromatography showed small amounts of unreacted 1-carbo-t-butoxypropan-2-one. Attempts to obtain additional conversion of the 1-carbo-t-butoxypropan-2-one by additional heating under reflux with a small amount of concentrated sulfuric acid did not significantly reduce the amount of the 1-carbo-t-butoxypropan-2-one. The reaction mixture was then evaporated to give an oil. The oil was chromatographed on silica gel (benzene eluant) to give the product as a yellow oil. The yellow oil was crystallized from hexane to give the product as a white solid, m.p. 68°-69°C. The infrared spectrum of the product showed α,β-unsaturated carbonyl absorption at 6.05μ. Elemental analysis showed: %S, calc. 11.38, found 11.22; %P calc. 11.02, found 10.78. The $LD_{50}$ (rats) of the product was 106–124 mg/kg.

EXAMPLE 4

Preparation of
O,S-dimethyl-N-[1-N'-phenylcarbamyl)prop-1-en-2-yl]phosphoroamidothioate

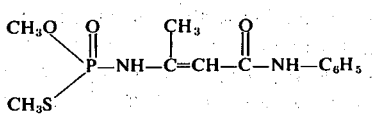

A solution of 7.1 g (0.005 mol) O,S-dimethylphosphoroamidothioate, 8.9 g (0.05 mol) 1-(N-phenylcarbamyl)propan-2-one, 0.1 g p-toluenesulfonic acid and 300 ml benzene was heated under reflux for 4 hours in a flask equipped with a Dean-Stark trap. The reaction mixture was evaporated to give a yellow oil. The oil was chromatographed on silica gel (hexane/methylene chloride eluants) to give the crude product. The product was crystallized from benzene/hexane to give a white solid, m.p. 103°-107°C. The infrared spectrum of the product showed α,β-unsaturated carbonyl absorption at 6.0μ. Elemental analysis showed: %S, calc. 10.66, found 10.48.

EXAMPLE 5

Preparation of
O,S-dimetyl-N-(1-carbethoxyprop-1-en-2-yl)phosphoroamidothioate

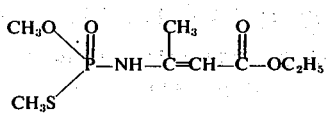

This compound was prepared by a procedure similar to that of Examples 1–4 from 0.07 mol O,S-dimethylphosphoroamidothioate and 0.14 mol 1-carbethoxypropan-2-one. The compound was an oil which showed α,β-unsaturated carbonyl absorption at 6.0μ. Elemental anaylsis showed: %S, calc. 12.7, found 13.0.

EXAMPLE 6

Preparation of
O,S-dimethyl-N-(3-detocyclohex-1-enyl)phosphoroamidothioate

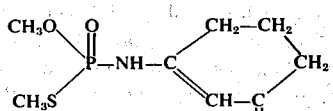

This compound was prepared by a procedure similar to that of Examples 1–4 from 0.077 mol O,S-dimethylphosphoroamidothioate and 0.077 mol 1,3-cyclohexanedione, The compound was a low-melting solid having α,β-unsatrated carbonyl absorption at 6.2μ. Elemental analysis showed: %S, calc. 13.6; found 12.8.

EXAMPLE 7

Preparation of
O,S-dimethyl-N-(1-benzoylprop-1-en-2-yl)phosphoroamidothioate

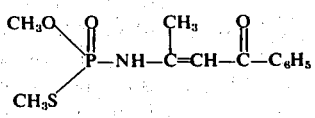

This compound was prepared by a procedure similar to that of Examples 1–4 from 0.063 mol O,S-dimethylphosphoroamidothioate and 0.065 mol 1-benzoylpropan-2-one. The compound was a yellow oil having α,β-unsaturated carbonyl absorption at 6.2μ. Elemental anaylsis showed: %S, calc. 11.2; found 12.1.

EXAMPLE 8

Preparation of
O,S-dimethyl-N-(1-carbomethoxyprop-1-en-2-yl)phosphoroamidothioate

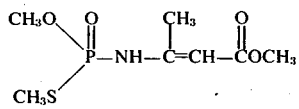

This compound was prepared by a procedure similar to that of Examples 1–4 4 from 0.075 mol O,S-dimethylphosphoroamidothioate and 0.077 mol 1-carbomethoxypropan-2-one. The compound was a yellow oil having α,β-unsaturated carbonyl absorption at 6.0μ. Elemental anaylsis showed: %S, calc. 13.4, found 12.8.

The phosphoroamidothioate reactant employed in Examples 1–8 may be suitably replaced by the compounds tabulated in Table I. Similarly, the dicarbonyl reactants employed in Examples 1–8 may be suitably replaced by the compounds tabulated in Table II. In Table II, φ represents phenyl. By way of illustration, with reference to Tables I and II, the reaction of compound Nos. b and 3 will produce a compound of the formula

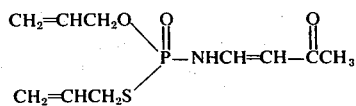

and the reaction of compound Nos. n and 4 will produce

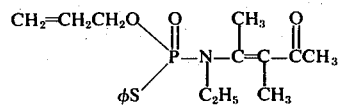

TABLE I

| No. | Compound |
|---|---|
| a | O,S-dihexylphosphoroamidothioate |
| b | O,S-diallylphosphoroamidothioate |
| c | O-propyl-S-allylphosphoroamidothioate |
| d | O-allyl-S-methylphosphoroamidothioate |
| e | O-phenyl-S-methylphosphoroamidothioate |
| f | O-ethyl-S-p-tolylphosphoroamidothioate |
| g | O-methyl-S-benzylphosphoroamidothioate |
| h | O-allyl-S-p-chlorobenzylphosphoroamidothioate |
| i | O-2,4-dichlorophenyl-S-methylphosphoroamidothioate |
| j | O-phenyl-S-p-bromophenylphosphoroamidothioate |
| k | O-butyl-S-(2-methyl-4-fluorophenyl)-phosphoroamidothioate |
| l | O,S-diethyl-N-methylphosphoroamidothioate |
| m | O,S-diallyl-N-isopropylphosphoroamidothioate |
| n | O-allyl-S-phenyl-N-ethylphosphoroamidothioate |
| o | O-p-nitrobenzyl-S-isopropyl-N-methylphosphoroamidothioate |

TABLE II

| No. | Compound | No. | Compound |
|---|---|---|---|
| 1 | $C_2H_5\overset{O}{C}CH_2\overset{O}{C}C_2H_5$ | 15 | $F_3C\overset{O}{C}CH_2\overset{O}{C}CF_3$ |
| 2 | $(n\text{-}C_5H_{11})\overset{O}{C}CH_2\overset{O}{C}CH_3$ | 16 | $Br_2CH\overset{O}{C}CH_2\overset{O}{C}CHBr_2$ |

TABLE II-continued

| No. | Compound | No. | Compound |
|---|---|---|---|
| 3 | $H\overset{O}{C}CH_2\overset{O}{C}CH_3$ | 17 | $C_2H_5\overset{O}{C}CH_2\overset{O}{C}O(p\text{-}F\phi)$ |
| 4 | $CH_3\overset{O}{C}\underset{CH_3}{\overset{}{C}H}\overset{O}{C}CH_3$ | 18 | $(i\text{-}C_3H_7)\overset{O}{C}CH_2\overset{O}{C}O\phi$ |
| 5 | $C_2H_5\overset{O}{C}CH_2\overset{O}{C}O(n\text{-}C_6H_{11})$ | 19 | $CH_3\overset{O}{C}CH_2\overset{O}{C}O(m\text{-}CH_3\phi)$ |
| 6 | $CH_3\overset{O}{C}CH_2\overset{O}{C}(p\text{-}Cl\phi)$ | 20 | $(n\text{-}C_6H_{11})\overset{O}{C}CH_2\overset{O}{C}NH_2$ |
| 7 | $CH_3\overset{O}{C}CH_2\overset{O}{C}(p\text{-}NO_2\phi)$ | 21 | $CH_3\overset{O}{C}CH_2\overset{O}{C}NH(CH_3)$ |
| 8 | $CH_3\overset{O}{C}CH_2\overset{O}{C}(O\text{—}CH_3\phi)$ | 22 | $CH_3\overset{O}{C}CH_2\overset{O}{C}N(CH_3)_2$ |
| 9 | $CH_3\overset{O}{C}CH_2\overset{O}{C}CH_2\phi$ | 23 | $C_2H_5\overset{O}{C}CH_2\overset{O}{C}NH(p\text{-}CH_3\Phi)$ |
| 10 | $CH_3\overset{O}{C}CH_2\overset{O}{C}CH_2(p\text{-}Br\phi)$ | 24 | (cyclopentane-1,3-dione structure) |
| 11 | $ClCH_2\overset{O}{C}CH_2\overset{O}{C}CH_2Cl$ | 25 | (5-trifluoromethyl-cyclohexane-1,3-dione structure) |
| 12 | $CH_3\overset{O}{C}CH_2\overset{O}{C}SCH_3$ | | |
| 13 | $ClCH_2\overset{O}{C}CH_2\overset{O}{C}SCH_3$ | | |
| 14 | $CH_3\overset{O}{C}CH_2\overset{O}{C}SC_2H_5$ | | |

UTILITY

The compounds prepared in Examples 1–8 were tested as follows to illustrate their insecticidal activity. Test results are reported in Table III.

TEST PROCEDURES

Cabbage looper (*Trichoplusia ni*): An acetone solution of the candidate toxicant containing a small amount of nonionic emulsifier was diluted with water to 500 ppm. Cabbage leaf sections were dipped in the toxicant solution and dried. The sections were then infested with cabbage looper larvae. Mortality readings were taken after 24 hours.

American Cockroach (*Periplaneta americana L.*): A 500-ppm acetone solution of the candidate toxicant was placed in a microsprayer (atomizer). A random mixture of anesthetized male and female roaches was placed in a container and 55 mg of the above-described acetone solution was sprayed on it. A lid was placed on the container. A mortality reading was made after 24 hours.

Housefly (*Musca domestica L.*): A 500-ppm acetone solution of the candidate toxicant was placed in a microsprayer (atomizer). A random mixture of anesthetized male and female flies was placed in a container and 55 mg of the above-described acetone solution was sprayed on it. A lid was placed on the container. A mortality reading was made after 24 hours.

Two-Spotted Mite (*Tetramuchus urticae*): An acetone solution of the candidate toxicant containing a small amount of nonionic emulsifier was diluted with water to 40 ppm. Pintobean leaves which were infested with mites were dipped in the toxicant solution. Mortality readings were taken after 24 hours.

Aphis (*Aphis gossypii* Glover): An acetone solution of the candidate toxicant containing a small amount of nonionic emulsifier was diluted with water to 40 ppm. Cucumber leaves infested with the cotton aphis were dipped in the toxicant solution. Mortality readings were then taken after 24 hours.

TABLE III

| Ex. No. | CABBAGE LOOPER (500 ppm) | AMERICAN COCKROACH (500 ppm) | HOUSEFLY (500 ppm) | MITE (100 ppm) | APHIS (40 ppm) |
|---|---|---|---|---|---|
| 1 | 0 | 100 | 100 | 15 | 15 |
| 2 | 100 | 100 | 100 | 0 | 70 |
| 3 | 60 | 100 | 100 | 15 | 22 |
| 4 | 20 | 90 | 100 | 22 | 30 |
| 5 | 100 | 100 | 100 | 96 | 98 |
| 6 | 50 | 100 | 100 | 100 | 94 |
| 7 | 40 | 3 | 100 | 100 | 10 |
| 8 | 50 | 100 | 100 | 100 | 100 |

The compounds of this invention are toxic to a variety of crop and household pests, in addition to the typical pests exemplified above. As most agricultural chemicals, they are not usually applied full-strength, but are generally incorporated with conventional biologically inert extenders or carriers normally employed for facilitating dispersion of active ingredients for agricultural chemical applications, recognizing the accepted fact that the formulation and mode of application may affect the activity of a material. The toxicants of this invention may be applied as sprays, dusts or granules to the insects or their environment or to hosts susceptible to insect attack. They may be formulated as granules of large particle size, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from 5–80% toxicant, and the rest inert material, which includes dispersing agents, emulsifying agents, and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents used in agricultural formulations include, for example: the alkyl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils; fatty acid esters of polyhydric alcohols and the ehtylene oxide addition products of such esters; and the addition products of long-chain mercaptans and ethylene oxide. Many other types of useful surface-active agents are available in commerce. The surface-active agent, when used, normally comprises from 1% to 15% by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the toxicant with a liquid or solid emulsifying agent, or may also contain a liquid carrier, such as xylene, heavy aromatic naphthas, isophorone, and other nonvolatile organic solvents. For application, these concentrates are dispersed in water or other liquid carrier, and are normally applied as a spray to the area to be treated.

Other useful formulations for insecticidal applications include simple solutions of the active ingredient in a dispersant in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover-up canopy. Baits, prepared by mixing solid or liquid concentrates of the toxicant with a suitable food, such as a mixture of cornmeal and sugar, are useful formulations for control of insect pests. Pressurized sprays, typically aerosols wherein the active ingredient is dispersed in finely divided form as a result of vaporization of a low-boiling dispersant solvent carrier, such as the Freons, may also be used. All of these techniques for formulating and applying the active ingredient are well known in the art.

The percentages by weight of the toxicant may vary according to the manner in which the composition is to be applied and the particular type of formulation, but in general comprise 0.5 to 95% of the toxicant by weight of the pesticidal composition.

The pesticidal compositions may be formulated and applied with other active ingredients, including other nematocides, insecticides, fungicides, bactericides, plant growth regulators, fertilizers, etc. In applying the chemical, an insecticidally effective amount and concentration of the toxicants of this invention are, of course, employed.

The terms "insecticide" and "insect" as used herein refer to their broad and commonly understood usage rather than to those creatures which in the strict biological sense are classified as insects. Thus, the term "insect" is used not only to include small invertebrate animals belonging to the class *Insecta*, but also to other related classes of arthropods whose members are segmented invertebrates having more or fewer than six legs, such as spiders, mites, ticks, centipedes, worms, and the like.

What is claimed is:

1. A compound of the formula

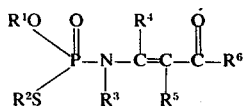

wherein $R^1$ and $R^2$ individually are alkyl of 1 to 6 carbon atoms or alkenyl of 3 to 6 carbon atoms; $R^4$ is hydrogen, alkyl of 1 to 6 carbon atoms or haloalkyl of 1 to 6 carbon atoms and 1 to 3 fluorine, chlorine or bromine; $R^3$ and $R^5$ individually are hydrogen or alkyl of 1 to 6 carbon atoms; $R^6$ is alkoxy of 1 to 6 carbon atoms, alkylthio of 1 to 6 carbon atoms, phenoxy,- phenoxy substituted with 1 to 2 alkyl of 1 to 4 carbon atoms, fluorine, chlorine or bromine, amino, N-lower alkylamino of 1 to 7 carbon atoms, N, N-di-lower alkylamino of 2 to 10 carbon atoms, N-phenylamino or N-lower alkylphenylamino of 1 to 7 carbon atoms.

2. The compound of claim 1 wherein $R^3$ is hydrogen.

3. The compound of claim 2 wherein $R^1$ is alkyl of 1 to 6 carbon atoms, $R^2$ is alkyl of 1 to 6 carbon atoms, $R^4$ is alkyl of 1 to 6 carbon atoms and $R^5$ is hydrogen.

4. The compound of claim 3 wherein $R^6$ is alkoxy.

5. The compound of claim 4 wherein $R^1$, $R^2$ and $R^4$ are methyl and $R^6$ is ethoxy.

6. The compound of claim 4 wherein $R^1$, $R^2$ and $R^4$ are methyl and $R^6$ is methoxy.

7. The compound of claim 3 wherein $R^6$ is amino, N-lower alkylamino, N,N-lower alkylamino, N-phenylamino or N-lower alkylphenylamino.

8. The compound of claim 7 wherein $R^1$, $R^2$ and $R^4$ are methyl and $R^6$ is N,N-diethylamino.

9. The compound of claim 7 wherein $R^1$, $R^2$ and $R^4$ are methyl and $R^6$ is N-phenylamino.

* * * * *

UNITED STATES PATENT AND TRADEMARK OFFICE
CERTIFICATE OF CORRECTION

PATENT NO. : 3,965,218
DATED : June 22, 1976
INVENTOR(S) : Francis J. Freenor

It is certified that error appears in the above-identified patent and that said Letters Patent are hereby corrected as shown below:

Preamble Abstract should read --$R^1$ to $R^6$ are as defined--.

Col 1, line 45 should read --1 to 4--.

Col 1, line 54 should read --6-membered carbocyclic--.

Col 2, line 50 should read --(3- --.

Col 2, line 62 should read --heated under reflux--.

Col 3, line 30 should read --[1-(carbo--.

Col 3, line 63 should read --[1-(N'--.

Col 4, line 1 should read (0.05 mol)--.

Col 4, line 37 should read --3-Keto--.

Col 4, line 57 should read --(1- --.

Col 5, line 16 should read --1-4 from--.

Col 8, line 45 should read --cover-crop--.

Signed and Sealed this

Twenty-eighth Day of September 1976

[SEAL]

Attest:

RUTH C. MASON
Attesting Officer

C. MARSHALL DANN
Commissioner of Patents and Trademarks